United States Patent
Cartier et al.

(10) Patent No.: US 9,055,996 B2
(45) Date of Patent: Jun. 16, 2015

(54) METHOD OF RETRIEVING A BLOOD CLOT FILTER

(75) Inventors: William A. Cartier, Hampton, NY (US); Theodore J. Beyer, Queensbury, NY (US); William M. Appling, Granville, NY (US); Giorgio di Palma, Queensbury, NY (US)

(73) Assignee: AngioDynamics, Inc., Latham, NY (US)

( * ) Notice: Subject to any disclaimer, the term of this patent is extended or adjusted under 35 U.S.C. 154(b) by 533 days.

(21) Appl. No.: 12/508,175

(22) Filed: Jul. 23, 2009

(65) Prior Publication Data

US 2009/0287242 A1 Nov. 19, 2009

Related U.S. Application Data

(62) Division of application No. 11/625,723, filed on Jan. 22, 2007, now Pat. No. 8,475,488.

(60) Provisional application No. 60/760,600, filed on Jan. 20, 2006, provisional application No. 60/862,670, filed on Oct. 24, 2006.

(51) Int. Cl.
*A61M 29/00* (2006.01)
*A61F 2/01* (2006.01)

(52) U.S. Cl.
CPC ............ *A61F 2/01* (2013.01); *A61F 2002/011* (2013.01); *A61F 2002/016* (2013.01); *A61F 2230/005* (2013.01); *A61F 2230/0067* (2013.01); *A61F 2230/0093* (2013.01)

(58) Field of Classification Search
CPC ............... A61F 2/01; A61F 2002/011; A61F 2002/016; A61F 2230/0093; A61F 2230/005; A61F 2230/0067

USPC .......... 606/200, 113, 191, 194; 128/899, 898
See application file for complete search history.

(56) References Cited

U.S. PATENT DOCUMENTS

| 4,425,908 | A | | 1/1984 | Simon |
| 4,494,531 | A | | 1/1985 | Gianturco |
| 4,688,553 | A | | 8/1987 | Metals |
| 4,832,055 | A | | 5/1989 | Palestrant |
| 5,133,733 | A | | 7/1992 | Rasmussen et al. |
| 5,344,427 | A | | 9/1994 | Cottenceau et al. |
| 5,810,874 | A | * | 9/1998 | Lefebvre ........................ 606/200 |
| 5,976,172 | A | * | 11/1999 | Homsma et al. .............. 606/200 |
| 6,217,600 | B1 | | 4/2001 | DiMatteo |

(Continued)

FOREIGN PATENT DOCUMENTS

EP 1258228 5/2002

OTHER PUBLICATIONS

PCT International Search Report for PCT/US07/60866 dated Oct. 19, 2007.

*Primary Examiner* — Tuan V Nguyen
*Assistant Examiner* — Tin Nguyen
(74) *Attorney, Agent, or Firm* — Peter J Flora

(57) ABSTRACT

A compact retrievable blood clot filter has a filter section, a releasable lock and an alignment section connected to the filter section. Alignment ribs of the alignment section have releasable upstream ends that are locked to the filter by the releasable lock. The releasable upstream ends of the alignment ribs are capable of being released from the releasable lock so that during retrieval of the filter, the alignment ribs can slide through the endothelial tissue that may have grown around the alignment ribs.

17 Claims, 15 Drawing Sheets

(56) References Cited

U.S. PATENT DOCUMENTS

| | | | |
|---|---|---|---|
| 6,267,776 B1 * | 7/2001 | O'Connell | 606/200 |
| 6,273,901 B1 | 8/2001 | Whitcher et al. | |
| 6,306,163 B1 | 10/2001 | Fitz | |
| 6,331,183 B1 * | 12/2001 | Suon | 606/200 |
| 6,391,045 B1 | 5/2002 | Kim et al. | |
| 6,506,205 B2 | 1/2003 | Goldberg et al. | |
| 6,881,218 B2 | 4/2005 | Beyer et al. | |
| 7,147,649 B2 | 12/2006 | Thomas | |
| 7,279,000 B2 | 10/2007 | Cartier et al. | |
| 2001/0000799 A1 | 5/2001 | Wessman et al. | |
| 2002/0138097 A1 | 9/2002 | Ostrovsky et al. | |
| 2003/0130680 A1 * | 7/2003 | Russell | 606/200 |
| 2003/0212432 A1 * | 11/2003 | Khairkhahan et al. | 606/200 |
| 2004/0193209 A1 * | 9/2004 | Pavcnik et al. | 606/200 |
| 2004/0230220 A1 | 11/2004 | Osborne | |
| 2005/0080449 A1 * | 4/2005 | Mulder | 606/200 |
| 2006/0241675 A1 * | 10/2006 | Johnson et al. | 606/200 |

\* cited by examiner

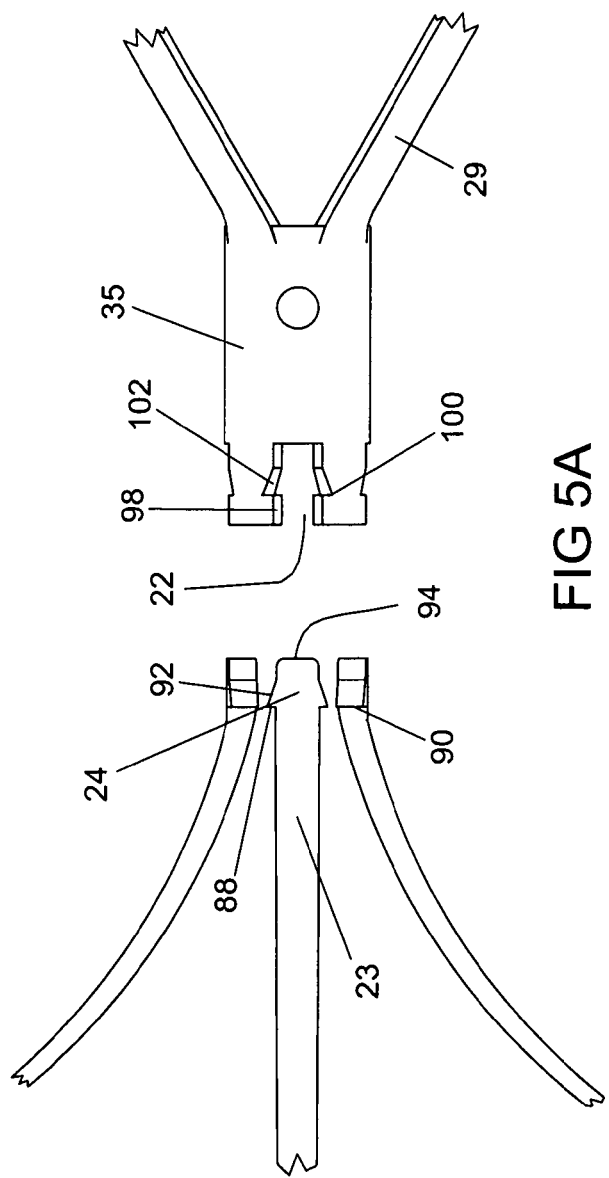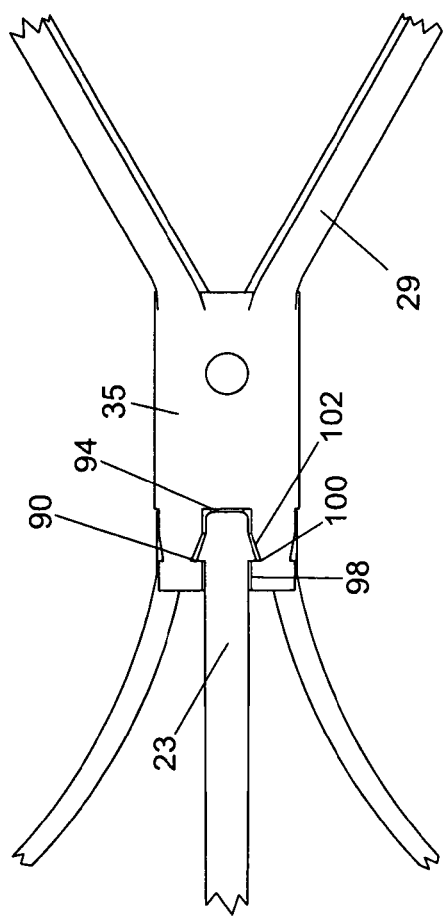

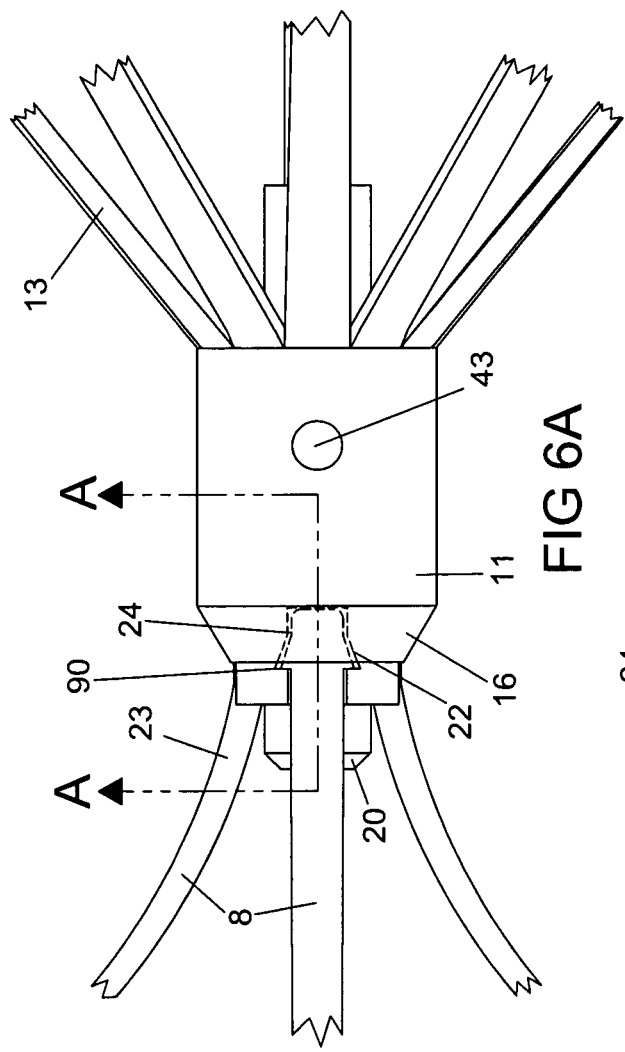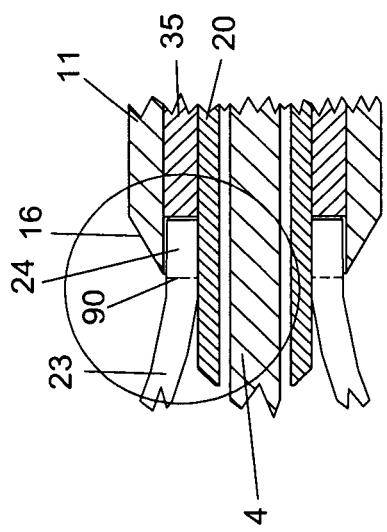

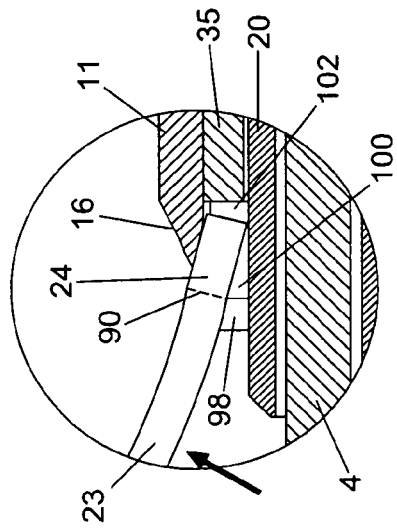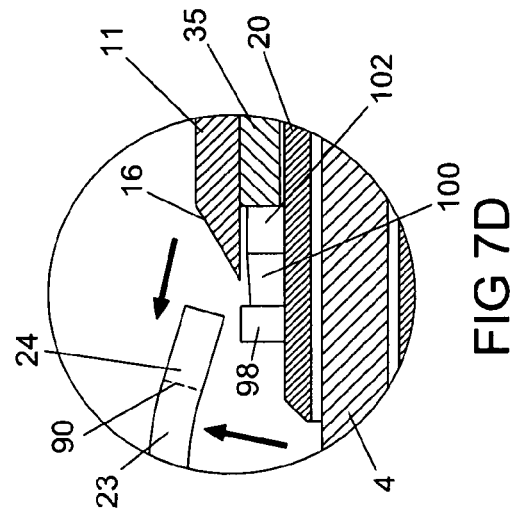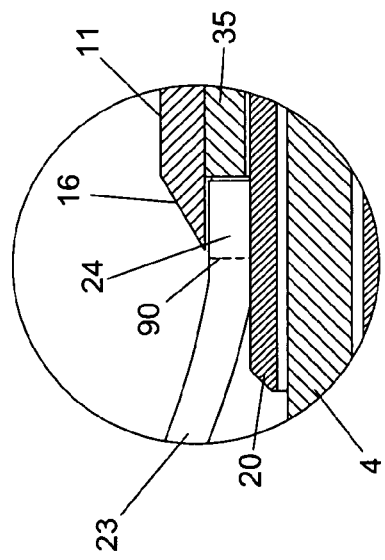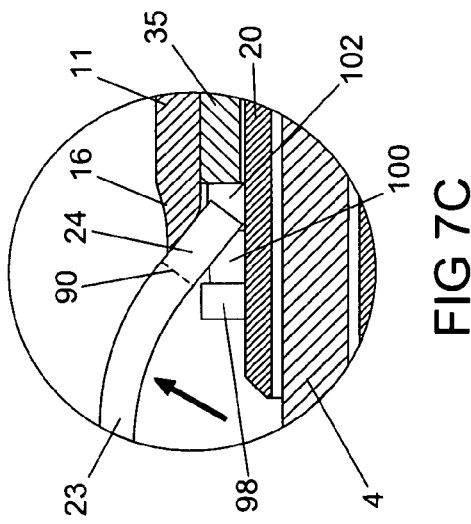
FIG 7

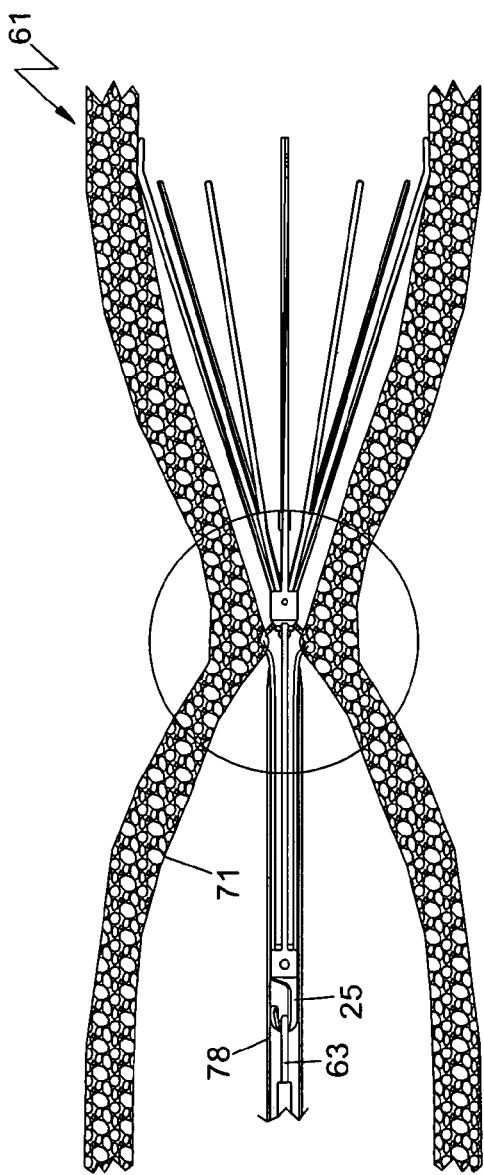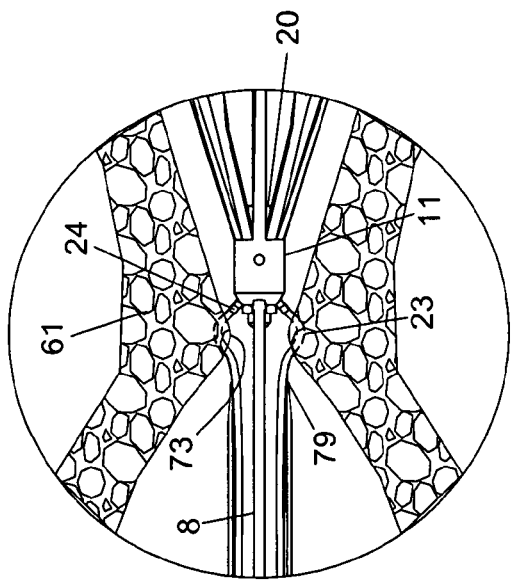

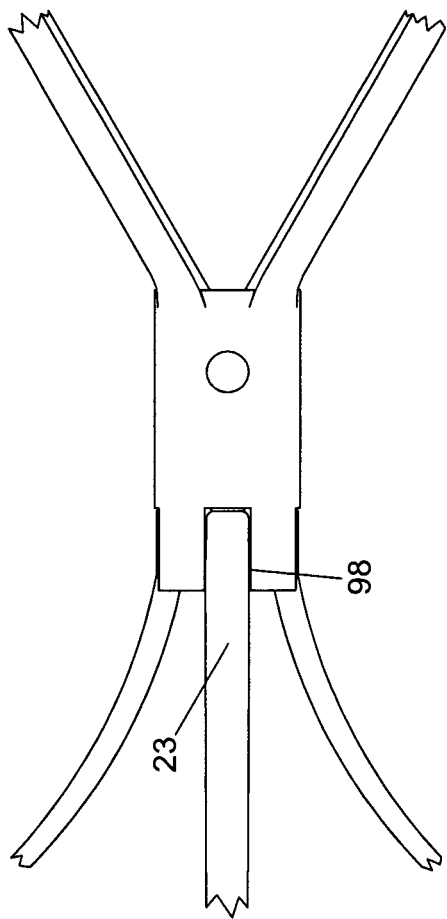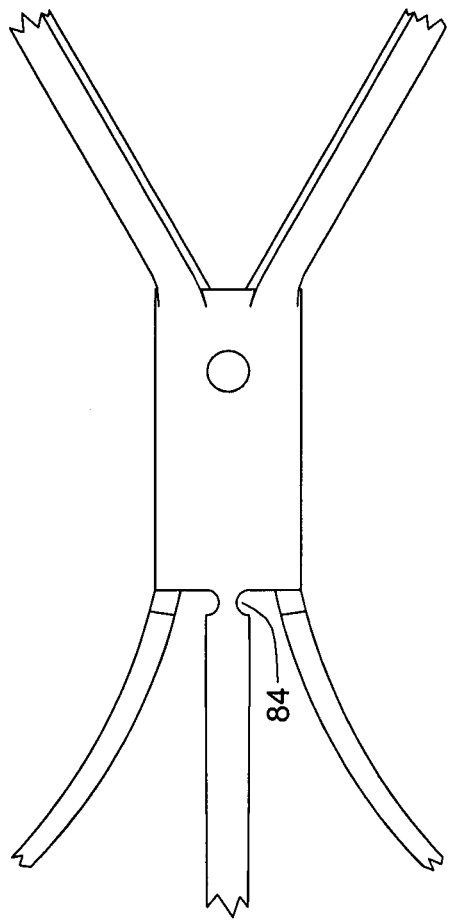

METHOD OF RETRIEVING A BLOOD CLOT FILTER

CROSS-REFERENCE TO RELATED APPLICATIONS

This is a divisional application of U.S. application Ser. No. 11/625,723 now U.S. Pat. No. 8,475,488, filed Jan. 22, 2007, which claims priority to U.S. provisional patent application Ser. No. 60/760,600 filed on Jan. 20, 2006 and U.S. provisional patent application Ser. No. 60/862,670 filed on Oct. 24, 2006, all of which are incorporated herein by reference in their entireties.

FIELD OF THE INVENTION

The present invention relates to a medical device apparatus and method for the capturing of thrombus. More particularly, the present invention relates to a retrievable vena cava filter device and a method of retrieving the same from a vessel.

BACKGROUND OF THE INVENTION

Vena cava filters are used to capture potentially fatal blood clots at an anatomical location where they may pose less risk of pulmonary emboli for the patient. Since the vast majority of pulmonary emboli originate from the lower body, filters are mainly placed in the inferior vena cava.

The optimal filter device should capture blood clots while ensuring continued blood flow through a blood vessel of a patient. Studies have demonstrated that a conical filter configuration provides optimal filtering efficiency. Conical designs force clots toward the center of the filter, allowing blood flow passage around the clot. Continued blood flow through the filter when a clot load is present ensures that captured clots are exposed to the lysing action of the blood flow.

Although conical filter configurations currently available on the market provide optimal filtering capabilities, these designs are prone to tilting and misalignment. When not in proper alignment, filtering ability is compromised. The central conical portion of the filter may tilt to the extent that it becomes embedded in the vessel wall. In retrievable filter designs, a retrieval hook is typically located at the central apex of the filter cone. If the filter tilts, this may result in the retrieval hook coming in contact with the vessel wall, making retrieval efforts more difficult or even preventing removal of the filter device. Tilting may also cause disruption of laminar blood flow, decrease in lysing of captured clots, or thrombus build-up and occlusion of the filter.

To maintain alignment of conical filters, centering or alignment features have been incorporated into filter designs. Centering has been accomplished by the use of free arms that extend radially outward from the filter to contact the vessel wall at a plane spaced apart from the contact point of the filter legs. While free arm centering designs ensure that the conical filtering section generally remains centered within the vessel, these designs are disadvantageous in that the free arms are prone to vessel perforation, fracture and in some cases misalignment due asymmetrical spacing of the free arms. Moreover, occasionally, when attempting to snare the alignment arms, they will become bent upwards making the retrieval of the filter even more difficult.

To overcome problems with free arm designs, closed loop alignment structures have been utilized. A closed loop alignment structure is comprised of alignment ribs that are connected at each end to a hub or other filter element and thus have no free standing arms. The non-perforating curved portion of each alignment rib may rest against the vessel wall to provide a centering function. These closed loop centering structures are less prone to fracture and will not perforate a vessel wall.

Although overcoming problems associated with free arm centering structures, filters designed with closed loop structures are difficult to retrieve from the vessel, particularly if a portion of the alignment structure has become incorporated into the vessel wall by endothelial overgrowth. Endothelial overgrowth may occur at any point where the filter contacts the vessel wall. Over time, the endothelial overgrowth may partially or completely encapsulate any portion of the filter in contact with the wall. This process is called neointimal hyperplasia and occurs as early as two weeks after implantation. The vessel wall responds to a foreign presence such as a filter by increased smooth muscle cell growth and neointimal thickening at the contact points. A band of endothelial tissue over a filter segment makes retrieval of the filter from the vessel more difficult, especially those filters designed with a closed loop configuration.

Accordingly, it is desirable to provide a retrieval blood clot filter with a filtering configuration and a centering structure that can be easily retrieved from the vessel even in the presence of endothelial growth over portions of the centering structure. The filter should be designed to allow percutaneous removal without significant trauma or damage to the vena cava wall even after neointima overgrowth has embedded those portions of the filter that are in contact with the vessel wall.

BRIEF SUMMARY OF THE DISCLOSURE

A retrievable blood clot filter according to one embodiment includes a filter section having a plurality of filter legs, a releasable lock and an alignment section coupled to the filter section. The alignment section includes alignment ribs having releasable upstream ends that are locked by the releasable lock. The releasable lock is capable of releasing at least one releasable upstream end of the alignment ribs so that during retrieval of the filter, the alignment ribs with their released upstream ends can slide through the endothelial tissue that may have grown around the alignment ribs.

In another aspect of the invention, a retrievable blood clot filter includes a conical filter section, a releasable lock, an alignment section and a shaft. The conical filter section has a filter hub and filter legs having downstream ends coupled to the hub and upstream ends that extend radially outwardly. The alignment section has an alignment hub and a plurality of alignment ribs having downstream ends coupled to the alignment hub and releasable upstream ends locked by the releasable lock. The alignment ribs extend radially outwardly from the downstream ends and then further extends radially inwardly in a cage like closed configuration. The releasable lock is capable of releasing the releasable upstream ends of the alignment ribs in response to a force applied to the releasable upstream ends during retrieval of the retrievable blood clot filter. The shaft couples the alignment hub to the filter hub even when all of the releasable upstream ends of the alignment ribs are released.

In another aspect of the present invention, a retrievable blood clot filter having a longitudinal axis is provided. The filter has a filter section, an alignment section and a releasable coupler disposed between the two sections. The alignment section has a plurality of alignment ribs and is spaced from the filter section along the longitudinal axis. The releasable coupler releasably holds the upstream ends of the alignment ribs.

In another aspect of the present invention, a blood clot filter including a conical filter section and an alignment section is provided. The conical filter section has a filter hub and a plurality of filter legs having downstream ends coupled to the hub and upstream ends that extend radially outwardly. The alignment section is spaced from the filter section along a longitudinal axis in a non-overlapping manner. The alignment section has an alignment hub and a plurality of alignment ribs having downstream and upstream ends. The alignment ribs extend radially outwardly from the downstream ends and then further extends radially inwardly.

In yet another aspect of the present invention, a method of retrieving a blood clot filter is provided, the filter having a filter section and an alignment section with the alignment section including a plurality of alignment ribs with each alignment rib having a releasable upstream end. To retrieve the filter, the alignment section is captured with a retrieval device and the releasable upstream ends of the alignment ribs are released. The filter with its released upstream ends of the alignment ribs is withdrawn into a retrieval sheath for removal.

These and various other objects, advantages and features of the invention will become apparent from the following description and claims, when considered in conjunction with the appended drawings. The invention will be explained in greater detail below with reference to the attached drawings of a number of examples of embodiments of the present invention.

BRIEF DESCRIPTION OF THE DRAWINGS

FIG. 5A is an enlarged partial view of the alignment section and secondary filtering hub prior to attachment according to the present invention.

FIG. 5B is an enlarged partial view of the alignment section and secondary filtering hub after assembly depicting the interlocking relationship between the alignment section and the secondary filtering hub.

FIG. 6A illustrates an enlarged partial plan view of the alignment ribs positioned within and being restrained within the primary filtering hub after final assembly.

FIG. 6B is an enlarged partial cross-sectional view of FIG. 6A taken along lines A-A.

FIG. 7 is a series of cross-sectional partial views of an alignment rib within the filtering hub illustrating the enlarged circled area of FIG. 6B.

FIG. 7A is a partial cross-sectional view of an alignment rib within the filtering hub prior to disengagement.

FIG. 7B is a partial cross-sectional view of an alignment rib during the first step of retrieval as force is applied to the upstream segment of the alignment rib.

FIG. 7C is a partial cross-sectional view of an alignment rib as additional force is applied and the alignment rib begins to disengage.

FIG. 7D is a partial cross-sectional view of an alignment rib after it has been released from the receiving pocket of the secondary filtering hub.

FIG. 10A is a plan view of the filter device, illustrating the retrieval sheath being advanced further into the vessel, thereby exerting pressure against the alignment ribs and causing the endothelial overgrowth covering the alignment rib contact portion to cinch inward toward the filter, according to the present invention.

FIG. 10B is an enlarged view of the circled area of FIG. 10A.

FIGS. 15A and 15B are plan views of alternative embodiments of the releasable lock and releasable upstream ends of the alignment ribs.

DETAILED DESCRIPTION OF THE INVENTION

For the purposes of the present application, the terms upstream and downstream refer to the direction of blood flow within a blood vessel. Accordingly, blood flows from an upstream direction towards a downstream direction. Also, it is important to note that although the filters disclosed herein are capable of being retrieved, they can be used as permanent filters without being retrieved.

Figure 1:
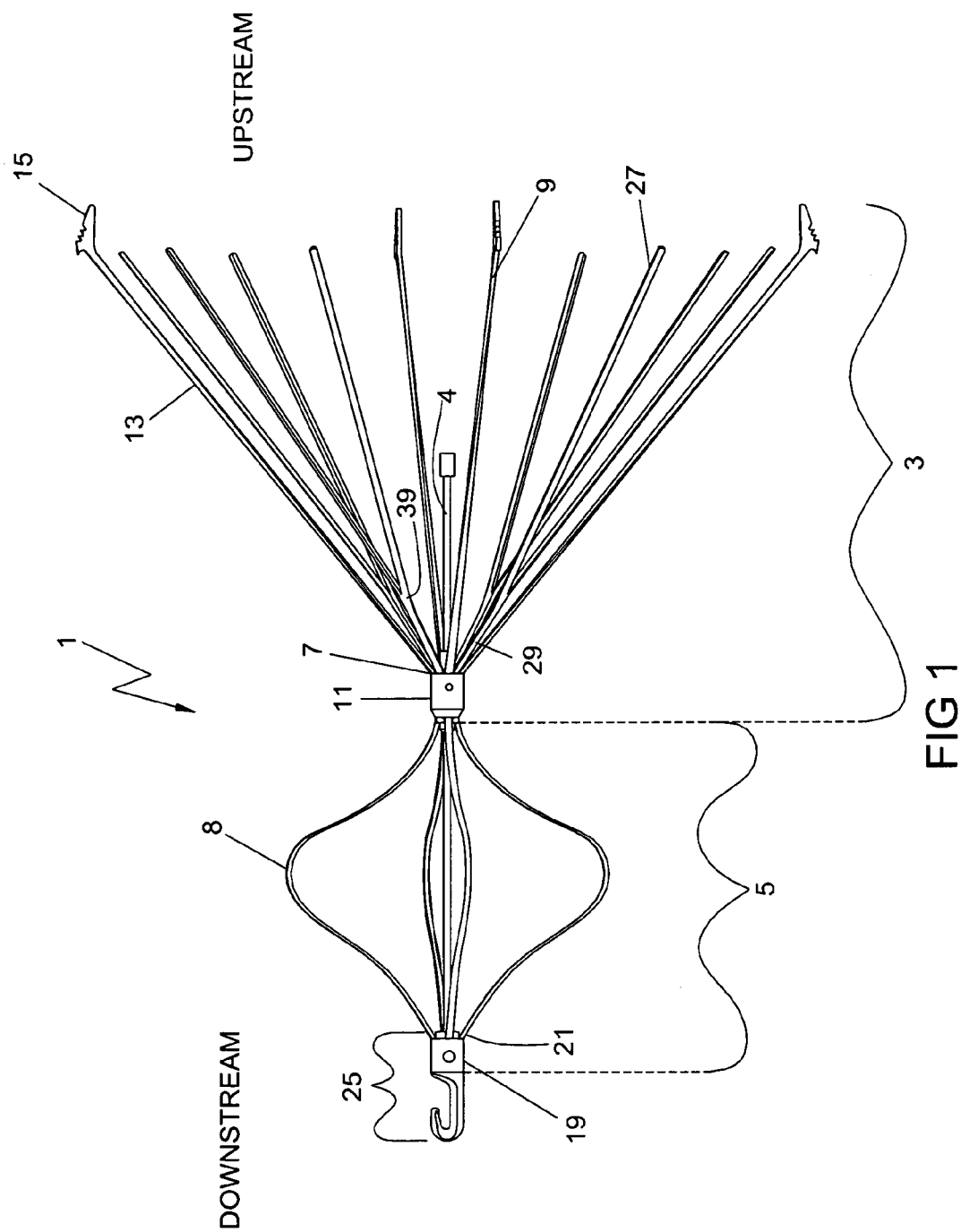
FIG. 1 is plan view of one exemplary embodiment of the vena cava filter device in an expanded state according to the present invention.

Referring to FIG. 1, there is shown an embodiment of the present invention in a plan view of an expanded vena cava filter device 1. When deployed in the path of the bloodstream, typically in the vena cava vein, the filter device 1 captures blood clots of a predetermined size and prevents them from traveling further downstream.

The vena cava filter device 1 is comprised of a conical filtering section 3, an alignment section 5, a center shaft/rod 4 and a retrieval hook subassembly 25. The conical filtering section 3 captures and lyses blood clots, anchors the filter device 1, and prevents the filter device 1 from migrating downstream. The alignment section 5 has a closed loop geometry (i.e., both ends of the alignment ribs 8 are attached to the filter 1) and provides central alignment of the conical filtering section 3 within the lumen of a vessel. The closed loop alignment section 5 also ensures that the conical filtering section 3 is maintained in proper longitudinal alignment relative to the alignment section 5. The center shaft 4 provides a moveable connection between the alignment section 5 and the conical filtering section 3 for retrieval. The retrieval hook subassembly 25 allows retrieval of the filter device 1 from the vessel using a snare device or other retrieval device known in the art.

In one embodiment, the conical filtering section 3 is comprised of a plurality of primary filtering legs 13 and secondary filtering legs 29. The primary filtering legs 13 having downstream ends 7 and upstream ends 9. Downstream ends 7 of the primary filtering legs 13 are connected to the primary filtering hub 11 and extend axially and radially outward from the primary filtering hub 11 to the upstream ends 9. Upstream ends 9 may be configured with vessel wall-engaging ends 15 such as barbs or other vessel anchoring mechanisms known in the art.

Each secondary filter leg 29 branches off into two branch legs 27 at a branch point 39 which is upstream of the filter hub 11. Unlike the primary filter legs 13, the upstream ends of the two branch legs of secondary filter legs 29 have a smooth profile without wall-engaging ends and are adapted to simply rest on a vessel wall.

The conical filtering section 3 captures clots and funnels the clots toward the conical primary filtering hub 11 which is located at the center of the vessel, where the clots are optimally exposed to the lysing action of the blood flow. The primary filtering hub 11 has an open configuration that includes a through lumen. This design is advantageous in that it minimizes blood flow turbulence while maintaining the structural integrity of the filter device 1.

The alignment section 5 provides central alignment of the conical filtering section 3 within the vessel. The alignment section 5 is formed of a plurality of alignment ribs 8 in a closed loop configuration. The downstream ends 21 of the alignment ribs 8 are permanently connected to the alignment hub 19, which is connected to the retrieval hook subassembly 25. The alignment ribs 8 extend radially outward from the alignment hub 19, form an arc, and then extend radially inward to the primary filtering hub 11 to form a closed loop. The alignment ribs 8 are securely positioned and interlocked within the primary filtering hub 11 until they are released during retrieval, as will be explained in more detail below.

As few as three alignment ribs 8 may be used to achieve centering of the filter device 1. In the deployed position the alignment section 5 is fully expanded to a cross-sectional diameter of approximately 18 mm, corresponding to the internal cross-sectional diameter less than that of the vessel. Accordingly, some or all of the alignment ribs 8 may rest against the vessel wall depending on vessel diameter. For vena cava vessels larger than 18 millimeters, the alignment ribs 8 will only contact the vessel wall if the filter device 1 begins to tilt away from the center of the lumen of the vessel. A filter placed in a vena cava that is less than 18 mm in diameter will contact the vessel wall with all alignment ribs 8. When the alignment ribs 8 contact the vessel wall, further tilting and misalignment of the filtering section 3 is prevented. Thus, alignment of the filtering section 3 within the vessel wall is achieved by alignment ribs 8 contacting the vessel wall, whether that contact is continual (as is the case for smaller diameter vessels) or occurs only when the filter device 1 begins to tilt (as is the case for larger diameter vessels).

The closed loop structure formed by the plurality of alignment ribs 8 avoids the problems associated with free-ended centering structures, which are prone to misalignment, tangling, and fracture. Misalignment may also cause the retrieval hook of prior art filters to become embedded in the vessel wall, making retrieval difficult or impossible. In contrast, the closed loop design of the present invention has no free ends when deployed and thus is not prone to misalignment or entanglement with other interventional devices.

The longitudinal moveable center shaft 4 and retrieval hook subassembly 25, illustrated in FIG. 1, provide a mechanism for easy retrieval of the filter device 1. The center shaft 4 extends from the alignment hub 19 through the primary filtering hub 11 terminating within the conical filter section 3 downstream of the filtering leg 13 ends 9. The primary filtering hub 11 will longitudinally slide along the center shaft 4 when force is applied to the retrieval hook subassembly, as will be explained in more detail below. Located at the downstream end of the filter device 1 and connected to the alignment hub 19, the retrieval hook subassembly 25 is configured to capture the end loop of a snare device during filter retrieval.

Figure 2:
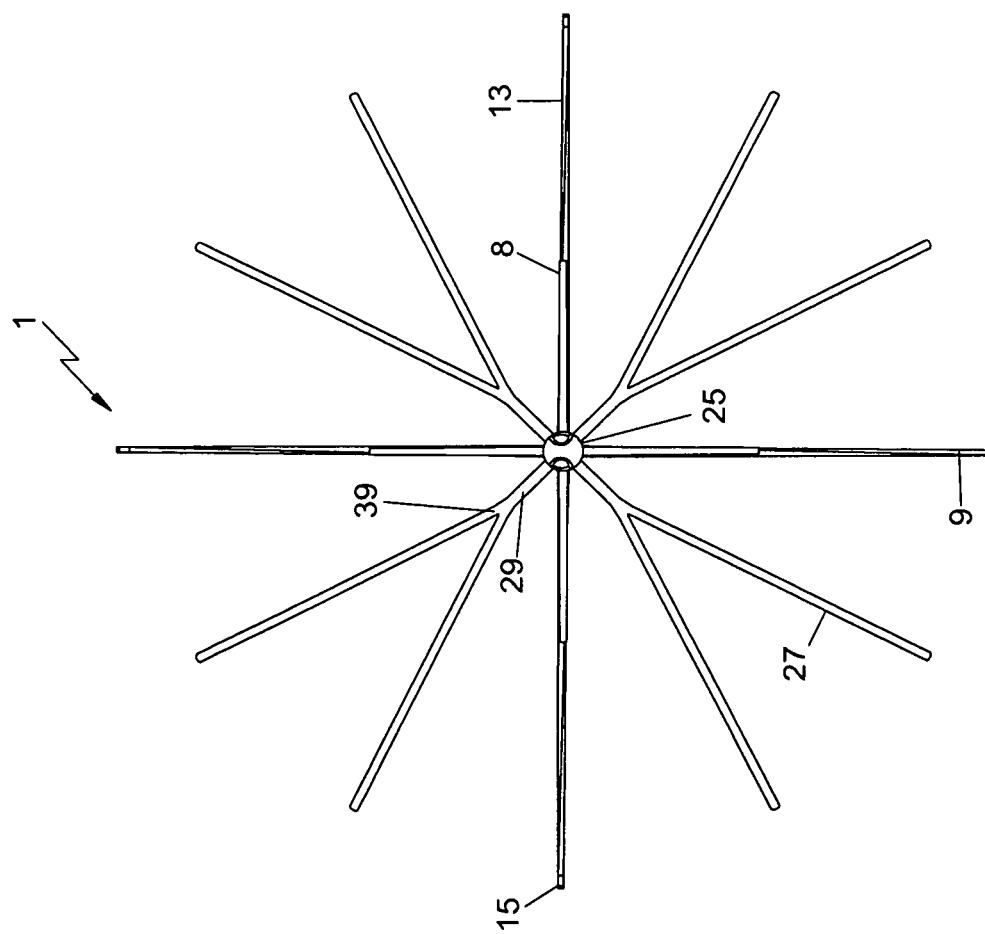
FIG. 2 is an enlarged downstream end view of the expanded vena cava filter device as illustrated in FIG. 1 according to the present invention.

Referring now to FIG. 2, a downstream end view of the filter device 1 in an assembled and expanded state is illustrated. Extending radially outward from the retrieval hook subassembly 25 are primary filtering legs 13 and secondary filtering legs 29. Anchoring ends 15 of the primary filtering legs 13 contact and engage the vessel wall, providing an attachment mechanism to prevent filter migration. Secondary filtering legs 29 also contact the vessel wall at a downstream location relative to the primary filtering legs 13.

The alignment ribs 8 are in axial alignment with the primary filtering legs 13 in a circumferential direction. With this configuration, the alignment ribs 8 do not provide unnecessary supplemental clot capturing. Instead, clots passing through the filtering section 3 will also pass freely through the alignment ribs 8. By allowing smaller, non-fatal clots to pass through the entire filter device 1, occlusion of the filter device 1 at the alignment section 5 is less likely. Downstream clot buildup in a filter results in blood flow turbulence and potential thrombi on the periphery of the vessel. By eliminating unnecessary secondary filtering, stable laminar blood flow is maintained, and captured clots can be effectively lysed within the center of the filtering section 3.

In the preferred embodiment, the fully expanded axial diameter of the filter device 1 at the upstream ends 9 is typically between 38-40 millimeters to accommodate larger cava diameters. The expanded filter 1 diameter will vary depending on the diameter of the patient's vena cava, which will partially constrain the expansion of filter 1, but may range from 18 to 23 millimeters for a typical patient. Although the angle of legs 13 proximate to the vessel wall may be reduced when under constraint from the vessel wall, the angle of the legs 13 relative to each other near the center of the vessel remains unchanged, as shown in FIG. 2. Specifically, the cross-sectional area between each secondary filter leg 29 from the downstream end 7 to the branch point 39 remains constant even when the relative angle between leg portion 27 and adjacent primary leg 13 has been decreased due to the constraint of the small vessel diameter. Although the branch legs 27 may move closer to adjacent filter legs 13 when constrained, the secondary leg 29 downstream of the branch point 39 remains in an unchanged position, i.e., the angle between each secondary leg 29 downstream of the branch point 39 relative to the longitudinal axis of the filter 1 does not change regardless of the vessel diameter. Thus, even when constrained within smaller diameter vessels, the filter 1 of the current invention maintains constant area coverage at the center of the vessel. As a result, the filter 1 is less likely to occlude when placed in a small vessel.

Still referring to FIG. 2, leg branches 27 do not individually connect to the filter hub 11. Rather, a set of two legs 27 merges into a single secondary leg 29, which then connects to the filter hub. Thus the secondary filter section provides an increased number of legs extending to the vessel wall for additional filter coverage at the outer circumferential area of the vein while minimizing the amount of filter material at the center of the vessel. Prior art filters with increased mass at the center of the filter have been shown to have increased filter occlusion rates. The design of this invention overcomes this problem by reducing the number of legs 29 that merge into the hub 11. As shown in FIG. 2, the reduced central area profile has only eight legs connecting to the filter at hub 11, with twelve leg ends contacting the vessel wall at an upstream location for enhanced filtering. The reduced mass at the hub area is also beneficial in that it minimizes non-laminar blood flow and turbulence near the center of the vessel. As a result, filter-induced thrombus build-up and comprised lysing is minimized.

Figure 3:
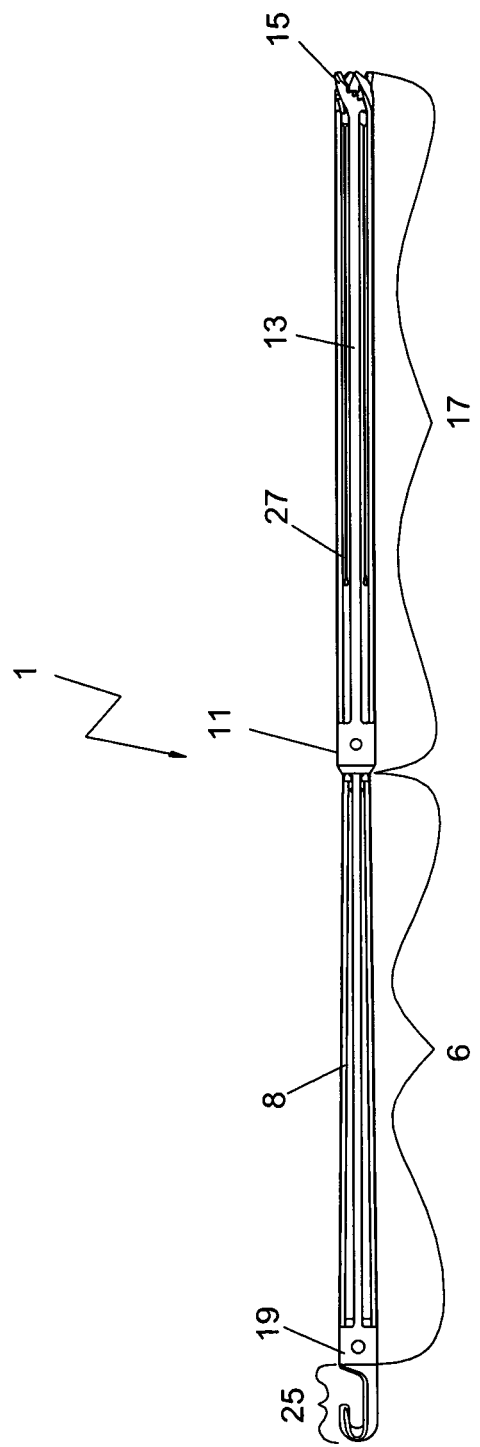
FIG. 3 is an illustration of the vena cava filter device in a non-expanded or collapsed state according to the present invention.

FIG. 3 is a side view of the filter 1 in an assembled, unexpanded state. The filter 1 is comprised of the hook subassembly 25, a first tubular body 6 which forms the alignment hub 19 and alignment ribs 8, and a second tubular body 17 forming the primary hub 11 and filtering legs 13. A third tubular body 18 (not visible in FIG. 3) is axially arranged within the second tubular body 17 and forms the secondary hub 35 and filtering legs 29 with their branch leg portions 27.

Each tubular body 6, 17 and 18 are preferably comprised of material with shape-memory characteristics, such as Nitinol, to allow expansion from a collapsed state illustrated in FIG. 3, to a deployed state at body temperature as illustrated in FIG. 1. Nitinol is an alloy well-suited for vena cava filters because of its shape-memory characteristics, which enables it to return to a pre-determined expanded shape upon release from a collapsed position. During manufacture of the filter device 1, the tubular bodies 6, 17, and 18 are first cut into the desired configurations using laser-machining techniques commonly known in the art. Other cutting techniques such as photo or acid etching may be used to form the desired cut patterns for the filter device 1.

Prior to final manufacturing assembly, the first tubular body 6 which forms the alignment section 5, is approximately 1.1 inches in length. The second tubular body 17, from which the primary filtering 3 is cut, is approximately 1.4 inches in length. When assembled as shown in FIG. 3, the combined length of tubular body 6 and 17 is approximately 2.5 inches, and the overall length of the device is 2.65 inches, including the assembled retrieval hook subassembly 25, which has an exposed hook portion of approximately 0.15 inches in length. The total filter 1 length of 2.65 inches shortens to approximately 2.15 inches after the filter 1 is expanded into the deployed state shown in FIG. 1.

The outer diameter of the first tubular body 6 and second tubular body 17 at their respective hubs are preferably 0.072 inches to accommodate insertion of the filter device 1 through a small sheath. Both tubular bodies have an inner diameter of 0.052 inches and a wall thickness of approximately 0.010 inches. The third tubular body 18, from which the secondary filtering section 26 is composed, has a length of approximately 1.3 inches, an outer diameter of approximately 0.051 inches, a wall thickness of approximately 0.009 to 0.010 inches, and an inner diameter of approximately 0.033 inches. These dimensions allow tubular body 18 to be inserted into the annular space of tubular body 17 during assembly.

After being laser cut, the first, second, and third tubular bodies 6, 17, and 18 are heat treated to form the final expanded filter device 1 configuration shown in FIG. 1. The filter device 1 may be polished before final assembly to provide a smooth outer surface finish using electro-polishing techniques or other methods commonly known in the art.

Thus, in one novel aspect of the invention, a filter device 1 is provided that has a separate alignment section 5 and a filtering section 3 that can be delivered through a small sheath. Although several prior art filters are sized to be delivered through a 6F sheath, these filters do not provide both centering and symmetrical conical filtering features. Prior art filters that do provide both centering and conical filtering capabilities generally require larger delivery devices due to the overlap of wire elements when the filter device 1 is in the collapsed state. By longitudinally separating the alignment section 5 and the conical filtering section 3 in a non-overlapping manner, the filter device 1 can be constrained in a delivery device that is substantially equal to the outer diameters of the first and second tubular bodies 6, 17. As an example, a filter fabricated from a tube with a 0.072 inch outer diameter will be able to be delivered using a sheath with an internal diameter as small as 0.075 inches, or within a 6 French sheath.

Figure 4:
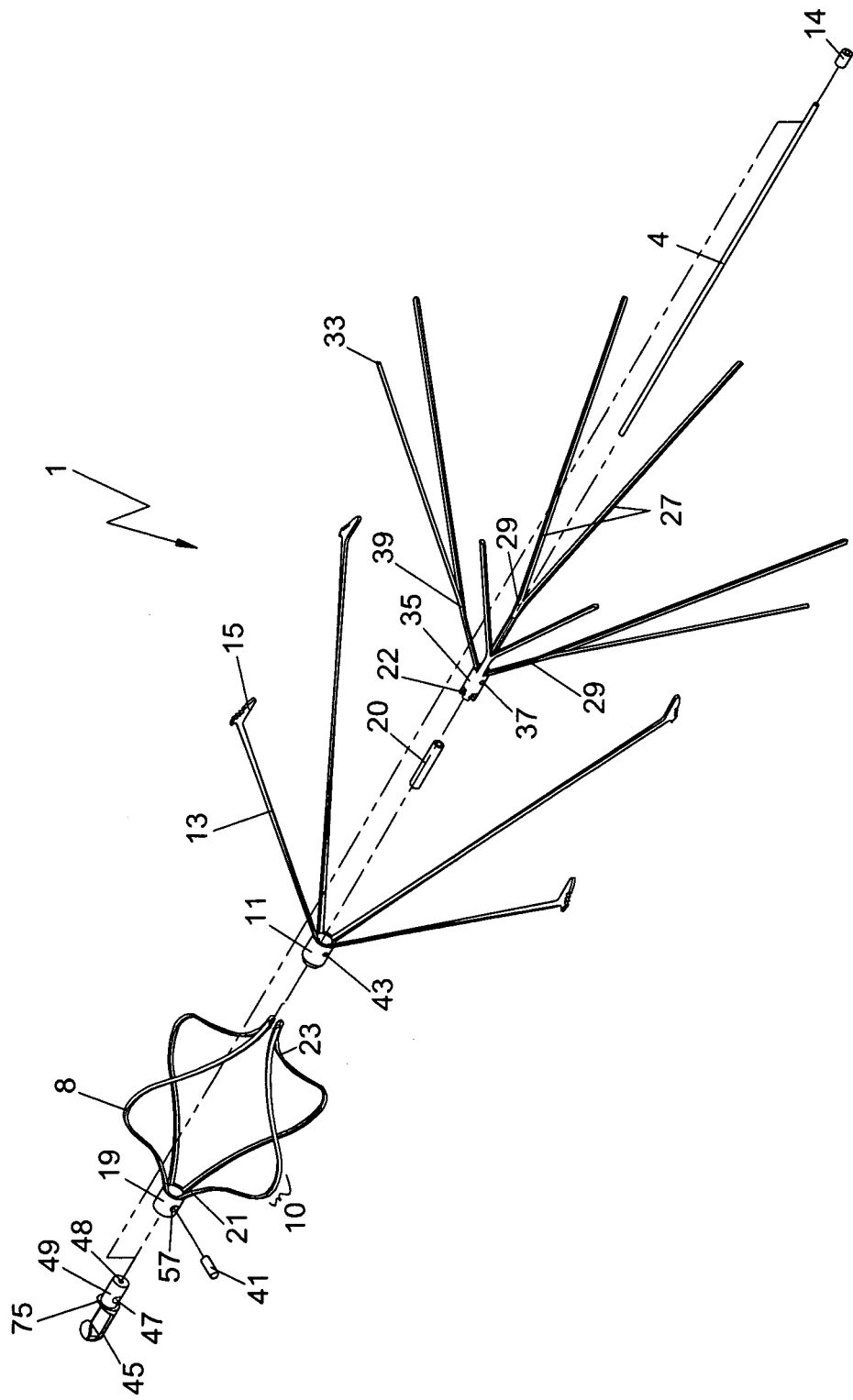
FIG. 4 is an exploded perspective view depicting the assembly of the components of the vena cava filter of the present invention.

The assembly steps of the filter device 1 are illustrated in FIG. 4. To assemble the filter device 1, a center spacer 20 is first inserted into and welded to the secondary filtering hub 35. The center spacer 20 is a hollow tubular structure made of Nitinol or other similar material. The center spacer 20 lumen is approximately 0.020" with an outer diameter of 0.032" to allow insertion of the spacer 20 into the through lumen of secondary filtering hub 35, which is dimensioned at approximately 0.033"Weld hole 37 facilitates welding of the center spacer 20 to the secondary filtering hub 35.

The center spacer 20 performs the dual function of a spacer and a stopper mechanism. The center spacer 20 ensures that the center shaft 4, when inserted through the spacer 20 lumen, is maintained in a centered position within the secondary filtering hub 35 lumen. The center shaft 4 has an outer diameter of approximately 0.015" which fits freely within the 0.020" inner diameter of the center spacer 20, allowing the center shaft 4 to move freely in a longitudinal direction relative to the vessel without becoming misaligned and off-center. The center spacer 20, in conjunction with stop member 14, also provides a travel stop feature by preventing the upstream end of center shaft 4 from moving completely through the spacer 20 lumen during retrieval.

The combined secondary filtering hub 35/center spacer 20 subassembly is then inserted into the lumen of primary filtering hub 11 as shown by the dotted line. The outer diameter of secondary filtering hub 35 is approximately 0.051" to allow ease of insertion into the primary filtering hub 11 lumen which has a diameter of 0.052". The secondary filtering hub 35 with spacer 20 is inserted into the lumen of the primary filtering hub 11, and then welded together using weld hole 43. With this method and configuration, the filtering section 3 maintains an outer diameter in an unexpanded state of 0.072".

The center shaft 4 is then attached to the hook subassembly 25. The hook subassembly 25 includes a hook insert section 49 formed of a solid cylindrical element extending in an upstream direction from the base section 45. A longitudinally arranged channel 48 is formed in the hook insert section 49. The center shaft 4 is inserted into channel 48 and welded in place.

The opposite end of center shaft 4 is passed through the alignment hub 19 lumen until the upstream edge of alignment hub 19 abuts against outer rim 75 of retrieval hook subassembly 25. Pin hole 57 of the alignment hub 19 and pin hole 47 of the hook subassembly 25 are brought into alignment with each other. A pin 41 is inserted through the aligned holes to secure the retrieval hook subassembly 25 and the alignment hub 19. The pin 41 is dimensioned so as to create an interference fit with the pin holes 57 and 47. The pin 41 may be made of any suitable material. Preferably, the pin 41 is at least partially made of Titanium, as illustrated in the preferred embodiment of the present invention. Pin 41 is of a length greater than the outer diameter of the alignment hub 19. For example, for a 0.072 inch alignment hub 19 diameter, the pin 41 may be 0.079 inches in length.

After the pin 41 is positioned within the aligned retrieval hook pin hole 47 and the alignment hub 19 pin hole 57, the connected retrieval hook subassembly 25 and the alignment hub 19 are placed in a swaging die and cold swaged to cause the outer surface of the pin 41 to be flush with the outer surface alignment hub 19. The swaging process also creates an interference fit between the pin 41 and the aligned pin holes 47 and 57, resulting in a strong, reliable attachment that does not require additional heating of the metal or welding, both of which may compromise the material of which the retrieval hook subassembly 25 and alignment hub 19 are composed.

The assembled filtering section 3 is then assembled to the alignment section 5 by inserting the downstream end of center shaft 4 through the lumen of center spacer 20 which was previously attached to the secondary filtering hub 35. Center shaft stop 14 is then welded to the downstream end of center shaft 4. The center shaft stop 14 prevents the filtering section 3 from becoming separated from the rest of the filter device 1 and ensures alignment of the filtering section 3 during retrieval. The center shaft 4 is stopped from additional downstream travel when the center shaft stop 14 comes into contact with the downstream end of the center spacer 20. The rod stop 14, which has a diameter of approximately 0.032" is too large to fit through the 0.020" of the spacer 20, and accordingly, is stopped from further downstream movement.

Although the shaft 4 disclosed herein with reference to FIG. 4 is a rigid rod, alternative designs are possible. For example, the shaft 4 may be comprised of a non-rigid material formed as a cable, wire or polymer connecting element. With this design, the connecting element 4 does not need to extend upstream of the primary filter hub 11.

The last assembly step is to insert the free upstream ends 23 of alignment ribs 8 into an interlocking relation with a releasable lock in the secondary filter hub 35. This last step is illustrated more clearly in FIGS. 5A-5B and 6A-6C. FIG. 5A and FIG. 5B depict partial further enlarged views of the interlocking relationship between the alignment ribs 8 and the secondary filtering hub 35. FIG. 5A illustrates the engaging tabs 24 at the upstream end of the alignment ribs 8 prior to insertion into the receiving pockets 22 of the secondary filtering hub 35. FIG. 5B depicts the interlocking relationship after the engaging tabs 24 have been locked by the releasable lock.

In the embodiment shown in FIGS. 5 and 6, the releasable lock (releasable coupler) is comprised of a plurality of spaced apart recesses/pockets 22 disposed at the downstream end of the filter hub 35, tapered forward segment (cover piece) 16 and center spacer 20. Each recess includes alignment rib receiving portion 98, two barb receiving sections (retaining surfaces) 100 and tapered portions 102.

The upstream end 23 of each alignment rib 8 of alignment section 5 is laser cut in a pattern forming an engaging tab 24. Each engaging tab 24 formed at the upstream end 23 of the alignment rib 8 includes a pocket engaging surface (projecting surface) 88, barb extensions 90, inwardly tapered sections 92 and a downstream face 94. The engaging tab 24 profile includes the two pocket engaging surfaces 88 that extend outwardly from the upstream end 23, and barb extensions 90. Barb extensions 90 form an expanded width of approximately 0.022 inches relative to the width of upstream ends 23, which are 0.016 inches. Engaging tab 24 also include two inwardly tapered sections 92 which terminate in downstream engaging face 94. When inserted into receiving pocket 22 of hub 35 as shown in FIG. 5B, the projecting surfaces 88 of barb extension 90 with its expanded width is retained by the retaining surfaces 100 to prevent axial movement and disengagement of engaging tab 24 from receiving pocket 22. In other words, the engaging tabs 24 at the upstream end of the alignment ribs 8 are locked by the releasable lock (22, 98, 100, 102).

Receiving pocket 22 of hub 35 is dimensioned to receive engaging tab 24 in an interlocking relationship, as shown in FIG. 5B. Alignment rib receiving portion 98 is dimensioned at 0.018 inches to allow upstream end 23 of rib 8, which is 0.016 inches, to be positioned within pocket 22 snugly, but without interference. Similarly, barb receiving section 100 is dimensioned at 0.026 inches in width to freely accommodate pocket engaging surfaces 88 and barb extensions 90, while simultaneously preventing disengagement of tab 24 when the alignment rib 8 is under axial force. Taper portion 102 of the receiving pocket 22 is dimensioned to be approximately 0.001 inch larger than the corresponding tapered section 92 of engaging tab 24 to allow a small clearance between the components without allowing movement.

FIG. 6A illustrates an enlarged partial plan view of the alignment ribs 8 positioned within and being restrained within the primary filtering hub 11 after final assembly and expansion of filter 1. FIG. 6B is a partial cross-sectional view of FIG. 6A taken along lines A-A. Each alignment rib 8 with corresponding engaging tab 24 is positioned within receiving pocket 22. The engaging tab 24 is held securely in position between the center spacer 20 and the tapered forward segment (cover piece) 16 of the primary filtering hub 11 which circumferentially surrounds and covers the engaging tabs 24. In the embodiment shown in FIG. 6A, the engaging tabs have an uncovered portion between the retaining surface 100 and the downstream end of the cover 16 in an axial direction to facilitate the release of the tabs during retrieval as will be discussed later herein in detail. Thus, the releasable alignment ribs 8 are restrained from movement in an inwardly radial direction by the center spacer 20 and restrained from movement in an outwardly radial direction by the inner wall of the segment 16. As previously discussed, the alignment rib 8 is also prevented from movement in an axial direction by the profile of the receiving pocket 24, which prevents movement of the barb extension 90.

Accordingly, in one aspect of the invention, an implantable, retrievable filter 1 is provided that will not release from a closed loop to an open loop structure under normal body movements experienced during implantation due to the interlocking design. The device 1 provides for central alignment within the vessel using a closed loop configuration that will not perforate the vessel wall, become entangled or fracture.

The present invention also pertains to a method of retrieving the implanted filter device 1 of the present invention from a vessel of a patient body. This method utilizes the alignment ribs' releasing feature to facilitate removal under those conditions in which filter portions have been encapsulated in endothelial overgrowth. The method involves inserting a retrieval sheath into the vessel, capturing the filter retrieval hook subassembly with a snare, advancing the retrieval sheath over the alignment ribs, thereby applying a prying force to release the alignment ribs from the filtering hub, and sliding the free rib ends through the overgrowth and into the sheath. The method further involves the steps of further advancing the retrieval sheath over the filtering section thereby capturing the filter legs within the sheath and removing the retrieval sheath and filter 1 from the vessel.

Figure 8:
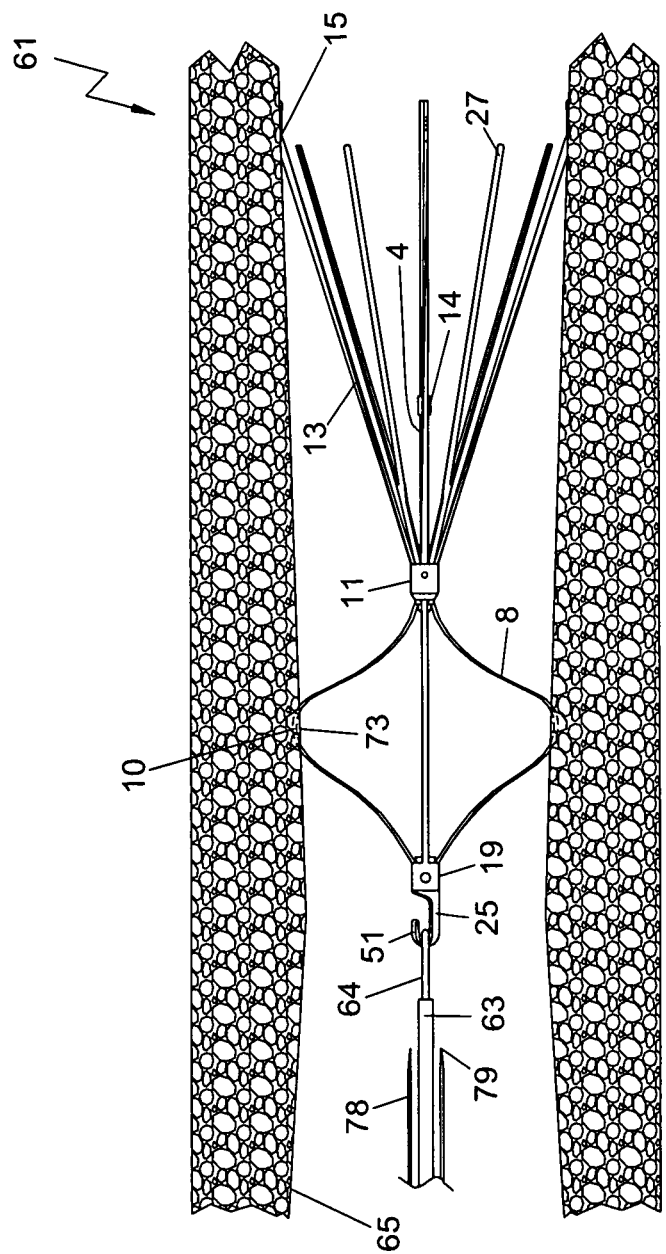
FIG. 8 is a side view of the filter device in a deployed state inside a vessel with a snare device attached to the hook of the filter device before retrieval, according to the present invention.

The retrieval steps of this method are illustrated in FIGS. 8 through 13 and also with reference to FIG. 7A-7D. FIGS. 7A-7D represent the circled area of FIG. 6B and illustrate the sequence of steps by which the engaging tab 24 is released by retrieval forces during removal of the filter 1 through endothelial tissue. FIG. 8 depicts a side view of the filter device 1 in an expanded state inside of a vessel 61 at the beginning of the filter device 1 retrieval process.

In the deployed state the filter device 1 is in an expanded position in the vessel 61, as shown in FIG. 8. The alignment ribs 8 extend radially outward from alignment hub 19 to contact the vessel wall at alignment rib contact portions 10, before extending inwardly to the filtering hub 11 in a closed loop configuration. The alignment rib contact portions 10 of the alignment ribs 8 are shown encapsulated in the endothelial overgrowth band 73 of the vessel wall 65. The filter legs 13 extend radially outward from the primary filtering hub 11 to contact the vessel wall 65 at wall engaging ends 15. The secondary filtering legs 29 also extend radially outward from the filtering hub 11 to contact the vessel wall 65 at a separate plane from wall engaging ends 15. Alternatively, the secondary filtering legs 29 may extend to contact the vessel wall on the same plane as the primary filtering legs 13. Center shaft 4 extends along the longitudinal axis of the vessel from the alignment hub 19 through the alignment ribs 8 and filtering hub 11 terminating in center shaft stop 14.

During implantation and prior to retrieval of the filter 1, the engaging tabs 24 of each alignment rib 8 are held within the receiving pockets 22 of the secondary hub 35, as previously described. An enlarged partial cross-sectional view of the engaging tabs 24 in an engaged position is shown in FIG. 7A. In the absence of a retrieval force, the engaging tab 24 remains constrained in this position by the center spacer 20, the receiving pocket 22, and the primary filtering hub 11.

To retrieve the filter device 1, a sheath 78 coaxially surrounding a snare device 63 is inserted into the vessel 61 and advanced to the filter 1. The snare device 63 is then advanced beyond the distal end 79 of the sheath 78, as shown in FIG. 8. The hook 51 of the retrieval hook subassembly 25 is captured by looping the snare wire 64 of the snare device 63 around the hook 51 and applying tension to securely engage the hook 51, as is well known in the art.

Figure 9A:
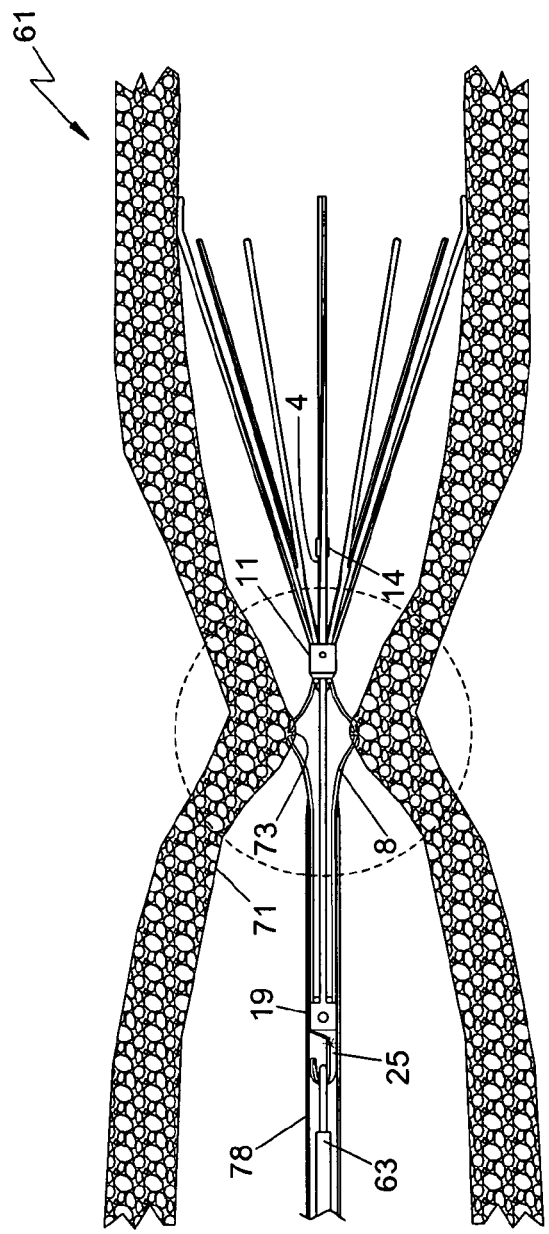
FIG. 9A is a plan view of the filter device with the alignment ribs partially collapsed and partially covered by endothelial tissue overgrowth at the alignment rib contact portion as the retrieval sheath is advanced over the alignment ribs, according to the present invention.
Figure 9B:
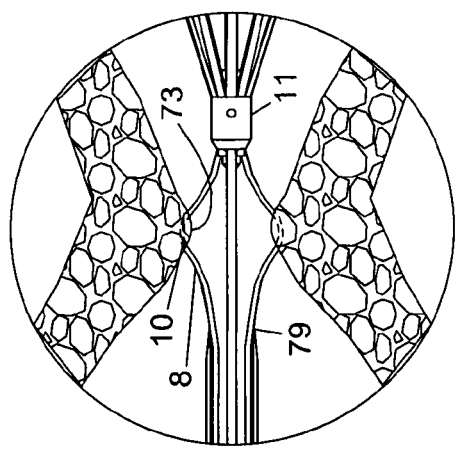
FIG. 9B is an enlarged view of the circled area of FIG. 9A.

Referring now to FIGS. 9A and 9B, tension is applied to the proximal end of snare device 63 in a downstream direction to draw the retrieval hook subassembly 25 and alignment hub 19 of the filter 1 into the sheath 78 lumen. Alternatively, the retrieval hook subassembly 25 and alignment hub 19 may be captured by advancing sheath 78 in an upstream direction while holding the snare device 63 stationary. As the downstream end of the filter 1 is drawn into the sheath 78 using either method, pressure is exerted upon the alignment ribs 8 by the distal end 79 of the retrieval sheath 78. This radially inward pressure forces the downstream ends 23 of the alignment ribs 8 begin to collapse and radially retract inward toward the center shaft 4 into a flattened position along the center shaft 4.

As previously described, the filtering hub 11 including the spacer 20 is slidably and coaxially mounted onto the center shaft 4. As the alignment ribs 8 collapse inwardly, they elongate and flatten out against the center shaft 4 as the shaft is pulled forward into sheath 78. The center shaft 4 thus functions to maintain axial alignment of both the alignment section 5 and the filtering section 3 during retrieval. The center shaft 4 also provides a central travel rail over which the alignment ribs 8 can elongate longitudinally without causing the filtering hub 11 to move.

The band of endothelial overgrowth 73 at the wall contacting portion 10 of the ribs 8 is illustrated in the enlarged view of FIG. 9B. As shown in this figure, the portion of the vessel 61 associated with the encapsulated alignment rib wall contacting portion 10 will be drawn inwardly toward the center of the vessel 61 as the alignment rib 8 begins to collapse. As the ribs 8 collapse inwardly, the band of endothelial overgrowth 73 is pulled inwardly and slides in an upstream direction along the alignment rib 8 toward the filtering hub 11.

As the alignment section 5 begins to collapse, the engaging tabs 24 are pushed radially outward from the central axis of the filter 1. This force, depicted by the arrow in FIG. 7B, is created by the band of endothelial overgrowth 73 which slides in an upstream direction along the alignment rib 8. The endothelial overgrowth 73 causes the upstream end 23 of the alignment rib 8 to bow outwardly. Specifically, the upstream portion 23 of the alignment rib 8 that is located within the alignment rib receiving portion 98 is pried away by this radially outward force created by the advancement of the endothelial band 73 toward the filtering hub 11. The barb extension 90 remains constrained within the barb receiving portion 100 of the receiving pocket as the upstream rib portion 23 begins to bow outwardly.

The tapered forward segment 16 of hub 11 may undergo a small amount of material deformation as pressure is applied by the engaging tab 24 against segment 16, causing it to flex slightly as tab 24 disengages from receiving pocket 22. The flexing of the hub forward segment 16 is illustrated in FIGS. 7B and 7C. If the filter 1 is constructed of Nitinol or other shape-memory material, segment 16 of primary filtering hub 11 will undergo deformation within the elastic limit, thus returning to its original shape after the alignment ribs 8 are released from the hub 11. Alternatively, the hub 11 may be made of material that will exceed the elastic limit when force is applied by the engaging tab 24, resulting in the segment 16 of hub 11 remaining in a slightly flexed position.

As illustrated in FIG. 10A, as the retrieval sheath 78 is further advanced toward the alignment rib contact portions 10, the outwardly directed force against the exposed portion of the alignment rib 8 increases further and causes the upstream end 23 of the rib 8 to flex and bow outwardly as shown in FIG. 7C. The force generated by the collapse of the alignment ribs 8 combined with the advancing endothelial tissue 73 acts as a lever, prying the engaging tab 24 out of the receiving pocket 22. As the alignment rib downstream end 23 bows outwardly, the barb extension 90 is moved both longitudinally upstream and radially outward, until the barb 90 is oriented such that it has sufficient clearance to disengage from the receiving pocket 22. Specifically, when barb extension 90 has been pushed to a point downstream and radially outward of barb receiving portion 100 by the force of the sliding endothelial band 73, the tapered portion of the engaging tab 92, which is of a smaller width than the barb extension 90, freely slides out of the receiving pocket 22.

Figure 11A:
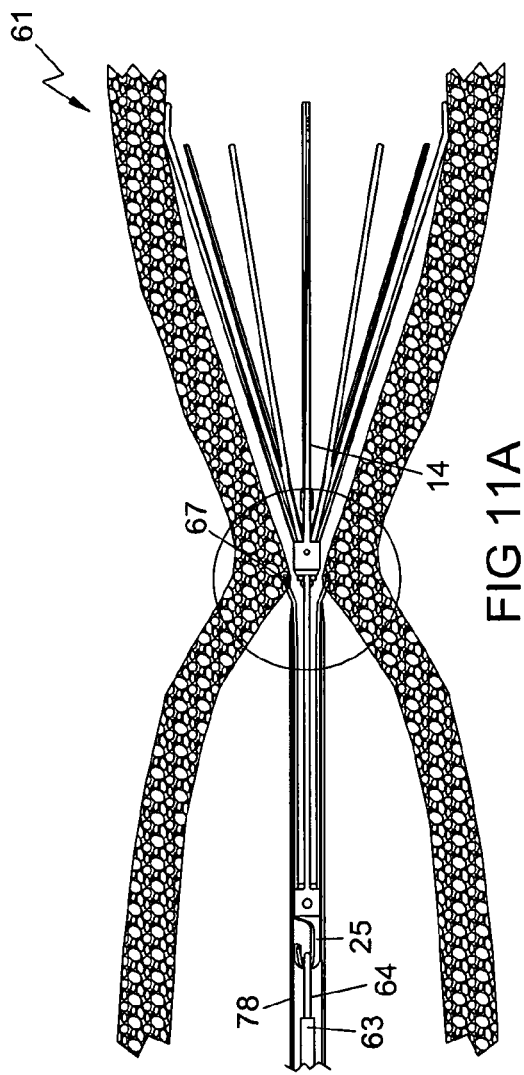
FIG. 11A is a plan view of the filter device, illustrating the alignment ribs spontaneously releasing from the filtering section, the alignment rib contact portion spontaneously releasing from the endothelial tissue overgrowth as the retrieval sheath is advanced toward the free ends of the alignment ribs, and the wall-engaging ends releasing from the vessel wall, according to the present invention.
Figure 11B:
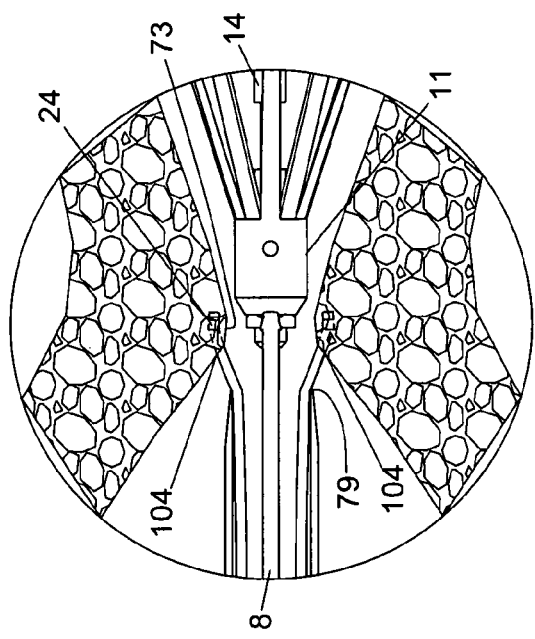
FIG. 11B is an enlarged view of the circled area of FIG. 11A.

FIGS. 11A and 11B depict the filter device 1 after the alignment ribs 8 have been completely released from the filtering hub 11, but prior to retraction of the rib 8 through the endothelial band 73. The radially outward force created by the endothelial band 73 along with the force created by the retraction of the snare 63 within the sheath 78 (depicted by the horizontal arrow in FIG. 7D) cause the engaging tab 24 to completely disengage from the receiving pocket 22. The vessel wall 65 remains partially collapsed by the alignment ribs upstream ends 23, which are disengaged from the filter 1, but remain encapsulated within the vessel wall 65. Except for the upstream ends 23, the alignment ribs 8 are completely collapsed, elongated against the center shaft 4 and constrained within the sheath 78.

A substantial length of the center shaft 4 is drawn into sheath 78, as shown by the position of the center shaft stop 14, which is advanced to just upstream of the filtering hub 11. The center shaft stop 14 prevents the center shaft 4 from moving completely through the primary filtering hub 11 and secondary filtering hub 35. As the center shaft stop 14 contacts and is restrained from further longitudinal movement by the filtering hub 11, any additional retrieval force placed on the filter 1 is carried by the center shaft 4 and stop 14, which together advance the filter 1 further into the sheath 78.

To disengage the alignment ribs 8 completely from the vessel wall 65, the snare wire 64 is further retracted. This movement causes the upstream ends 23 of the alignment ribs 8 be pulled through the endothelial overgrowth 73 in a downstream direction exiting through exit point 104. The upstream ends 23 of the ribs 8 are pulled through the overgrowth 73 at an angle that leaves only an opening 104, thus minimizing vessel trauma, and avoiding longitudinal tearing through the endothelial tissue 73. Thus, in one novel aspect of the invention, a method of filter retrieval is provided that is minimally traumatic to the vessel wall and does not cut through or otherwise damage the vessel 61.

Figure 12:
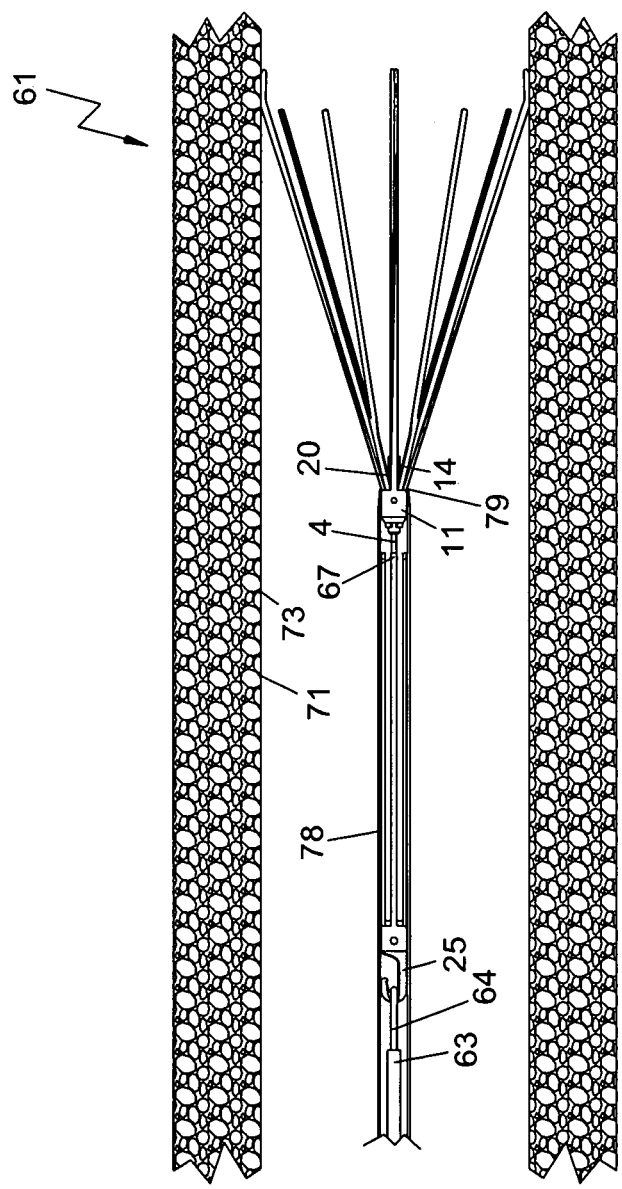
FIG. 12 is a plan view of the partially collapsed filter device inside of the vessel, according to the present invention.

Once the alignment ribs 8 are released from the vessel wall 65, the vessel wall 65 is no longer constrained by the filter 1 and the vessel 61 returns to its original shape, as shown in FIG. 12. As the retrieval sheath 78 is advanced, it completely encloses the alignment section 5 and the primary filtering hub 11. The primary filtering legs 13 and the secondary filtering legs 29 remain deployed, but begin to disengage from the vessel wall 65.

Figure 13:
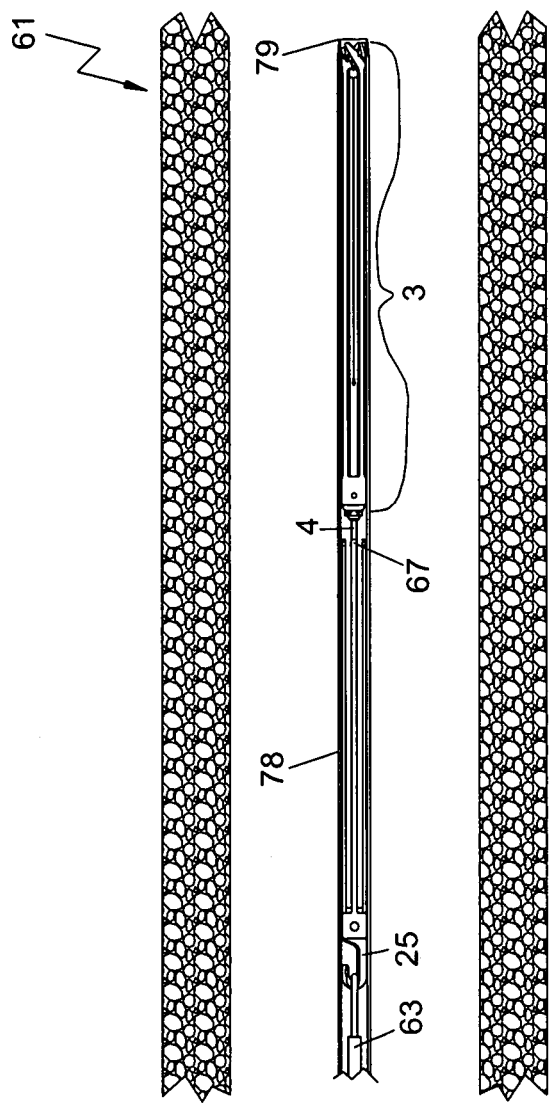
FIG. 13 is a plan view of the filter device in a completely collapsed state inside the retrieval sheath before being removed from the vessel.

Finally, as illustrated in FIG. 13, the sheath 78 is then further advanced over and completely encloses the plurality of primary filtering legs 13 and the secondary filtering legs 29. The filter device 1 becomes completely enclosed within the retrieval sheath 78. The entire collapsed filter device 1, along with the sheath 78 is then removed as a single unit from the blood vessel 61.

The method may also be used to retrieve a filter that had not been incorporated into the vessel wall 65. If there is no or minimal endothelial overgrowth 73, the radially outward prying force created by the band of endothelial tissue 73 as it slides upstream along the alignment rib 8 is not created. In the absence of this force, the alignment ribs 8 will collapse inwardly against the center shaft 4 but will not release from the filtering hub 11. Instead, the filter collapses in a linear fashion as previously described, with the alignment ribs 8 remaining captured within the filtering hub 11.

The method may also be effectively used to retrieve a vena cava filter 1 that has one or more but not all alignment ribs 8 encapsulated within endothelial bands 73 of tissue. In this aspect of the invention, those alignment ribs 8 that are encapsulated will release during retrieval due to the radially outward force created by the bands 73 as they slide upstream toward the filtering hub 11. Those alignment ribs 8 that have not been incorporated into the vessel wall 65 will flatten out against the center shaft 4 but will not undergo sufficient radially outward force to release from the filtering hub 11. Thus, in another novel aspect of the present invention, a retrievable filter 1 is provided that can be successfully retrieved in the absence or presence of vessel overgrowth on one or more alignment ribs 8.

Figure 14:
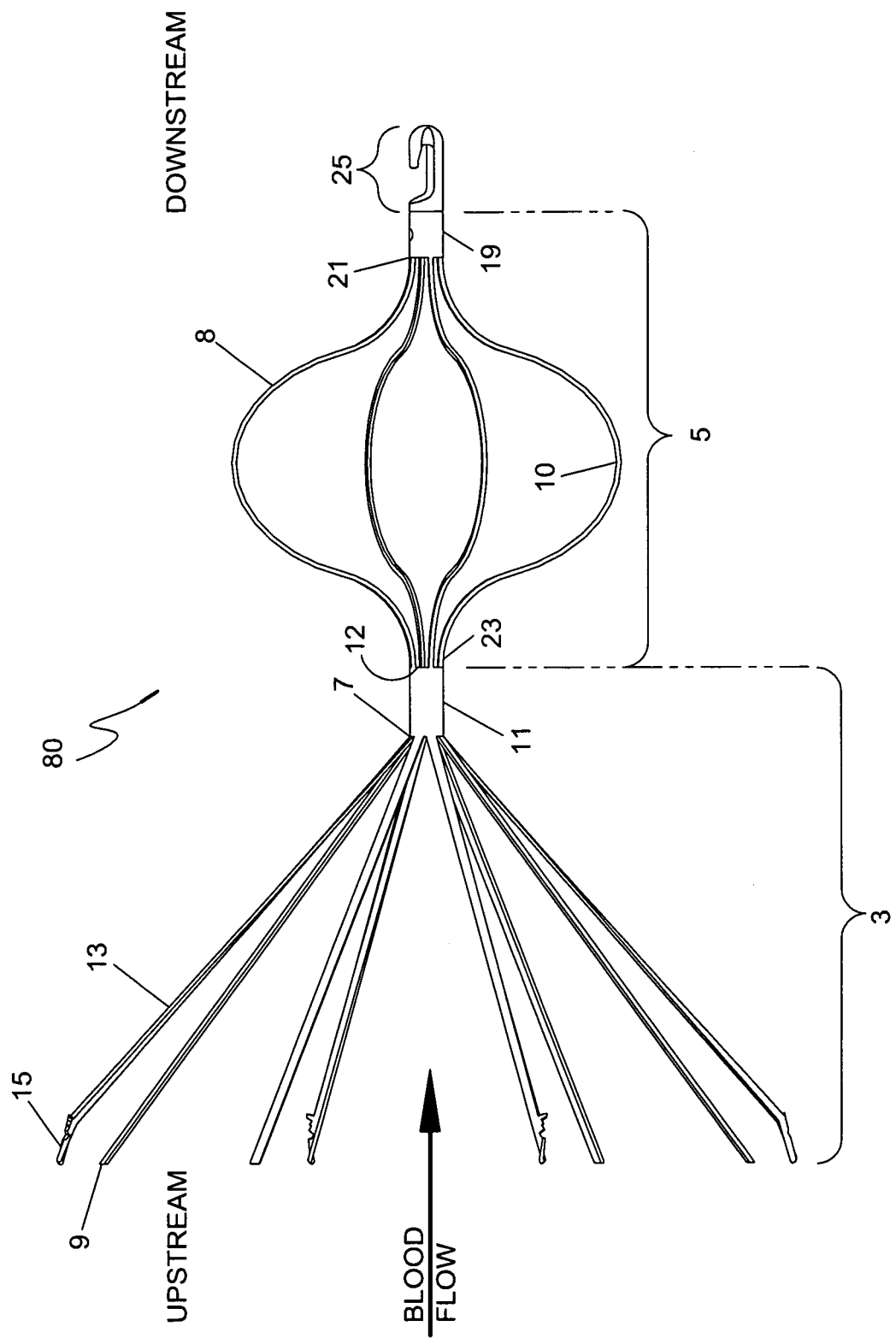
FIG. 14 is a plan view of an alternative embodiment of the retrievable filter device of FIG. 1.

FIG. 14 is a plan view of an alternative embodiment of the present invention. Similar to the device of FIG. 1, the retrievable filter device 80 includes a filter section 3 and an alignment section 5, except that the upstream ends of the alignment ribs 8 are fixedly attached to the filter hub 11. The alignment section 5 and filter section 3 are optimally comprised of a single tubular structure. Some of the filter legs 13 may include vessel wall-engaging ends 15 at their upstream ends while some may have a smooth profile without such wall-engaging ends at their upstream ends. Like previous embodiments, the filter section 3 and alignment section 5 are longitudinally spaced from one another in a non-overlapping relationship. This embodiment may be placed as a permanent implant or as short term retrieval device which is removed prior to significant overgrowth of vessel tissue, typically four to eight weeks. Optionally, the downstream end of the filter hub 11 may be sharpened to incise any tissue that may be present during retrieval. While FIG. 14 shows the filter legs 13 without any branches, the filter 80 can be provided with the primary filter legs 13 and secondary filter legs 29 each with two branch legs 27 as shown in FIG. 1.

The closed loop configuration of device depicted in FIG. 14 is advantageous over prior art filters with centering structures comprised of individual legs with free ends that are prone to entanglement and misalignment. In addition, the device is formed from a single Nitinol or other metallic tube with no welded joints. This construction is cost-effective and provides enhanced structural integrity and strength over welded devices. The single tube construction with the longitudinal separation of the alignment and conical filtering sections allows the device to be constrained within a smaller delivery system that is substantially equal to the outer diameter of the tube.

FIGS. 15A and 15B show alternative structures of a releasable lock and releasable upstream ends of the alignment ribs. As shown in FIG. 15A, the releasable lock may be designed to automatically release or weaken the coupling after a predetermined time has elapsed. As an example, the tapered forward segment (cover piece) 16 of the primary filtering hub 11 as shown in FIGS. 6A and 6B which circumferentially surrounds and covers the engaging tabs 24 may be comprised of a biodegradable material such as polyglycolide, polylactide, or other synthetic polymer commonly known in the art. The material is designed to gradually degrade and be absorbed by the body over a period of time, typically two weeks to six months, depending on the material formulation. During this period of time, the vessel wall contact points 10 of the filter will become incorporated into the vessel wall, thus stabilizing the filter within the vessel. Once the biodegradable material has been absorbed by the body, the engaging tabs 24 are no longer restrained and will disengage from hub 11 with relatively little force. The endothelial overgrowth at the vessel wall contact points of the filter immobilizes the alignment ribs preventing misalignment and migration of the device as well as perforation of the vessel by the ribs.

Alternatively, the releasable upstream ends 23 of the alignment ribs 8 can be permanently attached to the hub 11 and be made of biodegradable material at point 84 as shown in FIG. 15B. After a predetermined time period, the releasable upstream ends 23 of the ribs 8 will be released into open ends or will be sufficiently weakened so that the upstream ends 23 of the alignment ribs 8 will break with relatively little force. In this case, the filter hub 11 acts as the releasable lock.

In yet another embodiment, the releasable lock may be designed with releasable upstream ends 23 that are structurally weakened relative to the remaining portions of the alignment ribs 8 to deform or break under a predetermined retrieval force. The alignment ribs 8 may include releasable upstream ends 23 that have a reduced profile section as shown at 84 in FIG. 15B (either in width, thickness or both), which will deform or break at a lower retrieval force than the other filter components, thereby causing the alignment rib upstream ends 23 to be released from hub 11. Alternatively, the reduced profile of the upstream ends 23 can be a reduced thickness or width of the tabs 24 such that they will deform or break at a lower retrieval force than the other filter components. Another possibility is that the alignment ribs 8 may include releasable upstream ends 23 that have a reduced profile section at point 84 as in FIG. 15B and be made of biodegradable material at the same point 84.

In yet another embodiment of the releasable locking mechanism, the engaging tab 24 and the recess 22 may be laser cut so as to create an interference friction fit as shown in FIG. 15A. The engaging tabs which have a slightly larger profile than the receiving recesses 22, are forcibly inserted into the recesses. The material interference between each engaging tab 24 and recess 22 creates a friction fit which will release only under a retrieval force sufficient to overcome the retaining force. The advantage of this embodiment is that it does not rely on the endothelial overgrowth band to create a prying force. Instead the friction fit may be overcome by a direct longitudinal force.

Other configurations and methods of retrieving a vena cava filter 1 are also possible. Modifications of the details illustrated in this disclosure, including filter and component shapes, numbers, wall-engaging designs, dimensions, materials, methods of construction, and methods of use, are within the scope of this invention. For example, the number of filtering legs on both the primary and secondary filtering structures may be varied. The filter 1 may be assembled without utilizing a secondary filtering structure 26. The assembly methods, component dimensions and materials may be varied. In addition, the interlocking profiles of the alignment ribs 8 and filtering hub 11 may also be modified and remains within the scope of the present invention. Any engaging tab 24 and receiving pocket 22 profile may be used if it is configured to provide a holding force in an axial direction and allow release when an outwardly radial force is present. Tab shapes including circular, semi-circular, rectangular, teardrop or elliptical are within the scope of the invention. The center shaft 4 component may be of a variable length in a spring configuration or comprised of a non-metallic material such as a nylon wire. The center shaft 4 may be of any configuration that provides a travel path that exceeds the elongated length of the alignment section. Accordingly, the scope of the invention is not limited to the foregoing specification.

What is claimed is:

1. A method of retrieving a blood clot filter having a filter section and an alignment section having a plurality of alignment ribs with each alignment rib having a releasable upstream end, the method comprising:
    capturing the alignment section with a retrieval device, wherein the releasable upstream ends are locked by a releasable lock;
    retrieving the blood clot filter by pulling the retrieval device so a longitudinal force is applied to the filter by the retrieval device while the filter section and the alignment section are coupled to each other, wherein a radial force is applied to at least one of the releasable upstream ends of the alignment ribs encapsulated by endothelial growth thereby releasing the locked releasable upstream ends of at least one alignment ribs such that the at least one of the released upstream ends of the alignment ribs becomes free end and becomes free of the endothelial growth around the alignment ribs, wherein at least one of the remaining alignment ribs free from the endothelial growth remains locked; and
    withdrawing the blood clot filter into a retrieval sheath for removal of the filter.

2. The method of claim 1, wherein the step of retrieving includes applying the longitudinal force on the captured alignment section such that an endothelial tissue that surrounds the alignment ribs applies a force on the releasable upstream ends so as to release the upstream ends from the releasable lock.

3. The method of claim 1, wherein the step of retrieving includes pulling the captured alignment section such that the endothelial growth that surrounds the alignment ribs applies a radially outward force on the releasable upstream ends so as to release the upstream ends from the releasable lock.

4. The method of claim 1, wherein:
    the releasable upstream ends are friction fit with the releasable lock; and
    the step of retrieving includes applying a force on the releasable upstream ends to overcome a retaining force of the friction fit.

5. The method of claim 1, wherein:
    the releasable upstream ends of the alignment ribs include biodegradable material; and
    the step of retrieving includes letting the releasable upstream ends biodegradable over time to become the free ends.

6. The method of claim 1, wherein:
    the releasable upstream ends of the alignment ribs include biodegradable material; and
    the step of retrieving includes letting the releasable upstream ends biodegrade over time to weaken a coupling of the releasable upstream ends to the filter section.

7. The method of claim 1, wherein the step of capturing is performed after the step of retrieving.

8. The method of claim 1, wherein:
    the releasable upstream end of at least one alignment rib includes a structurally weakened portion; and
    the step of retrieving includes applying a force on the weakened portion to release the releasable upstream end.

9. The method of claim 1, wherein:
    the filter includes a shaft coupled to both the alignment section and the filter section, and positioned along a longitudinal axis of the alignment section; and
    the step of retrieving includes releasing the locked releasable upstream ends while the shaft couples the alignment section and the filter section.

10. The method of claim 1, wherein:
    the filter includes a shaft coupled to both the alignment section and the filter section, and positioned along a longitudinal axis of the alignment section;
    the shaft includes a stop member; and
    the step of retrieving includes releasing the locked releasable upstream ends while the shaft and the shaft stop member prevent the filter section from separating from the alignment section.

11. A method of deploying and retrieving a blood clot filter, the method comprising:
    deploying, inside a blood vessel, a blood clot filter having a filter section, a releasable lock and an alignment section coupled to the filter section and having a plurality of alignment ribs with each alignment rib having a releasable upstream end locked by the releasable lock, such that the alignment section self-expands into a deployed state while the releasable upstream ends are locked by the releasable lock;

inserting a retrieval sheath into the blood vessel;

capturing the alignment section with a retrieval device;

retrieving the blood clot filter by pulling the alignment section with the retrieval device so a longitudinal force is applied to the filter by the retrieval device while the filter section and the alignment section are coupled to each other, wherein any releasable upstream end of the alignment rib encapsulated by endothelial growth is forced away from the releasable lock thereby releasing the locked releasable upstream ends of the alignment ribs such that at least one of the released upstream ends of the alignment ribs becomes free end and becomes free of the endothelial growth around the alignment ribs, wherein at least one of the remaining alignment ribs free from the endothelial growth remains locked; and withdrawing the free upstream ends of the alignment ribs, the locked releasable upstream ends of the alignment ribs, and the filter section through the retrieval sheath for removal of the filter.

12. The method of claim 11, wherein the step of retrieving includes advancing the retrieval sheath over the alignment ribs.

13. The method of claim 11, wherein the step of capturing includes capturing a hook attached to a downstream end of the alignment section using a snare device.

14. The method of claim 11, wherein:

the releasable upstream ends are friction fit with the releasable lock; and the step of retrieving includes applying a force on the releasable upstream ends to overcome a retaining force of the friction fit.

15. The method of claim 11, wherein:

the releasable upstream ends of the alignment ribs include biodegradable material; and the step of retrieving includes letting the releasable upstream ends biodegrade over time to become the free ends.

16. The method of claim 11, wherein:

the filter includes a shaft coupled to both the alignment section and the filter section, and positioned along a longitudinal axis of the alignment section; and the step of retrieving includes releasing the locked releasable upstream ends while the shaft couples the alignment section and the filter section.

17. The method of claim 11, wherein:

the filter includes a shaft coupled to both the alignment section and the filter section, and positioned along a longitudinal axis of the alignment section;

the shaft includes a stop member; and the step of retrieving includes releasing the locked releasable upstream ends while the shaft and the shaft stop member prevent the filter section from separating from the alignment section.

* * * * *